United States Patent [19]

Ocleppo

[11] Patent Number: 6,049,585
[45] Date of Patent: Apr. 11, 2000

[54] NON-DESTRUCTIVE X-RAY INSPECTION APPARATUS FOR LIQUID FOODSTUFFS CONTAINED IN GLASS VESSELS OR BOTTLES

[75] Inventor: Rinaldo Ocleppo, Canale, Italy

[73] Assignee: Dylog Italia SpA, Italy

[21] Appl. No.: 09/075,475

[22] Filed: May 11, 1998

[51] Int. Cl.$^7$ .................................................. G01N 23/12
[52] U.S. Cl. .............................. 378/57; 378/58; 378/208
[58] Field of Search ................................ 378/57, 58, 51, 378/208; 250/223 R, 223 B, 559.4

[56] References Cited

U.S. PATENT DOCUMENTS

| | | | |
|---|---|---|---|
| 3,576,442 | 4/1971 | Nakamura | 250/223 B |
| 3,886,353 | 5/1975 | Shioya | 250/223 B |
| 3,958,078 | 5/1976 | Fowler et al. | |
| 4,025,202 | 5/1977 | Deane | 356/239.4 |
| 4,136,930 | 1/1979 | Gomm et al. | 250/223 B |
| 5,400,381 | 3/1995 | Steude et al. | 378/57 |

*Primary Examiner*—David P. Porta
*Attorney, Agent, or Firm*—Paul & Paul

[57] ABSTRACT

An apparatus for X-ray inspection of liquid foodstuffs contained in glass vessels such as jars or bottles, comprising a conveyor, along which a plurality of such vessels is moved, having a horizontal path, a section for the inlet and a section for the outlet of said vessels, and a device fitted along said horizontal path for inspecting said vessels and detecting the presence of contaminants in said liquid foodstuff. The apparatus provides for two arcuate connecting sections between said inlet and outlet sections, respectively. The connecting sections extend in vertical directions with the vessel advancing direction varying by 180° with respect to a horizontal axis, whereby said inspection device controls the vessels in an upturned position.

5 Claims, 2 Drawing Sheets

NON-DESTRUCTIVE X-RAY INSPECTION APPARATUS FOR LIQUID FOODSTUFFS CONTAINED IN GLASS VESSELS OR BOTTLES

BACKGROUND OF THE INVENTION

Field of the Invention

The present invention refers to an apparatus for non-destructive X ray inspecting of liquid foodstuff contained in glass vessels, jars, bottles or similar transparent containers.

This known kind of inspection aims to detect the presence of contaminants in a liquid foodstuff, where the word contaminant means a particle or fragment of a foreign substance having a specific weight higher than that of the foodstuff in which it is accidentally present, that can be for example a glass, metal or stone fragment.

It is well known that in most cases the non-destructive X-ray inspection of liquid foodstuffs in glass vessels o bottles is accomplished through an apparatus provided with a single inspection tube, and therefore with a single viwepoint suitably located with respect to the bottles. This known apparatus is generallly provided with an emitter and a sensor between which the articles to be inspected are moved in a row.

The invention will be illustrated in more details with reference to the inspection of bottles, but this is not to be meant as limiting the invention.

The bottoms of many bottles and glass vessels are inwardly curved, i.e. they have an inwards convexity that creates an annulus with side walls close to each other that is difficult to be inspected through X-ray devices, since a glass, metal or stone contaminant having a specific weight higher than that of the liquid inside the vessel or the bottle to be inspected settles on the vessel bottom. Because of the inwardly convexity of the vessel bottom, in the known inspection apparatus it is difficult to detect the contaminant by using a single viwepoint.

SUMMARY OF THE INVENTION

It is an object of the present invention to overcome the above illustrated limitations and drawbacks of the prior art devices, and more particularly by providing an apparatus allowing for a quick, simple and effective inspection of glass vessels and/or bottles.

This object is accomplished through the invention consisting of an apparatus for non-destructive X-ray inspection of liquid foodstuffs contained in glass vessels such as jars or bottles, comprising:

a conveyor along which a plurality of such vessels is moved, having a horizontal path, a section for the inlet and a section for the outlet of said vessels, and a device disposed along said horizontal path for inspecting said vessels and detecting the presence of contaminants in said liquid;

said conveyor further comprising a first arcuate section connecting said inlet section with said horizontal path and extending in a vertical direction with the vessel advancing direction varying by 180° with respect to a horizontal axis; and a second arcuate section connecting said outlet section with said horizontal path and extending in a vertical direction with the vessel advancing direction varying by 180° with respect to a horizontal axis;

said conveyor being further provided with means for holding the vessels even when these latter advance along a non-horizontal direction, said inspection device being disposed at a point of said horizontal path where said vessels are in an upturned position.

Further advantageous characteristics both of construction and use of the invention are recited in the dependent claims.

The apparatus according to the invention conveys the filled and closed bottles along a path that overturns them, i.e. that causes a 180° rotation of the advancing bottles with respect to their axes, and causes the bottles to pass before the inspection apparatus when they are upside-down (bottom up). Thus the X-ray examination takes places from the bottom, with the liquid completely resting on the tap, and this allows for a quick and accurate inspection of the liquid inside the bottle which is not negatively affected by the bottom shape.

A further characteristic of the invention resides in that the inspection unit is substantiallly located at the end of a rectilinear or straight conveyor section along which the bottles are conveyed upside-down. Preferably the inspecting device is located at a distance from the end of the rectilinear path that is a function of the viscosity of the liquid inside the bottles, since this parameter affects the sinking speed of the contaminant in the liquid.

BRIEF DESCRIPTION OF THE DRAWINGS

The invention will now be disclosed with reference to the attached drawings relating to a preferred but non limiting embodiment, in which.

DETAILED DESCRIPTION OF A PREFERRED EMBODIMENT

Figure 1:
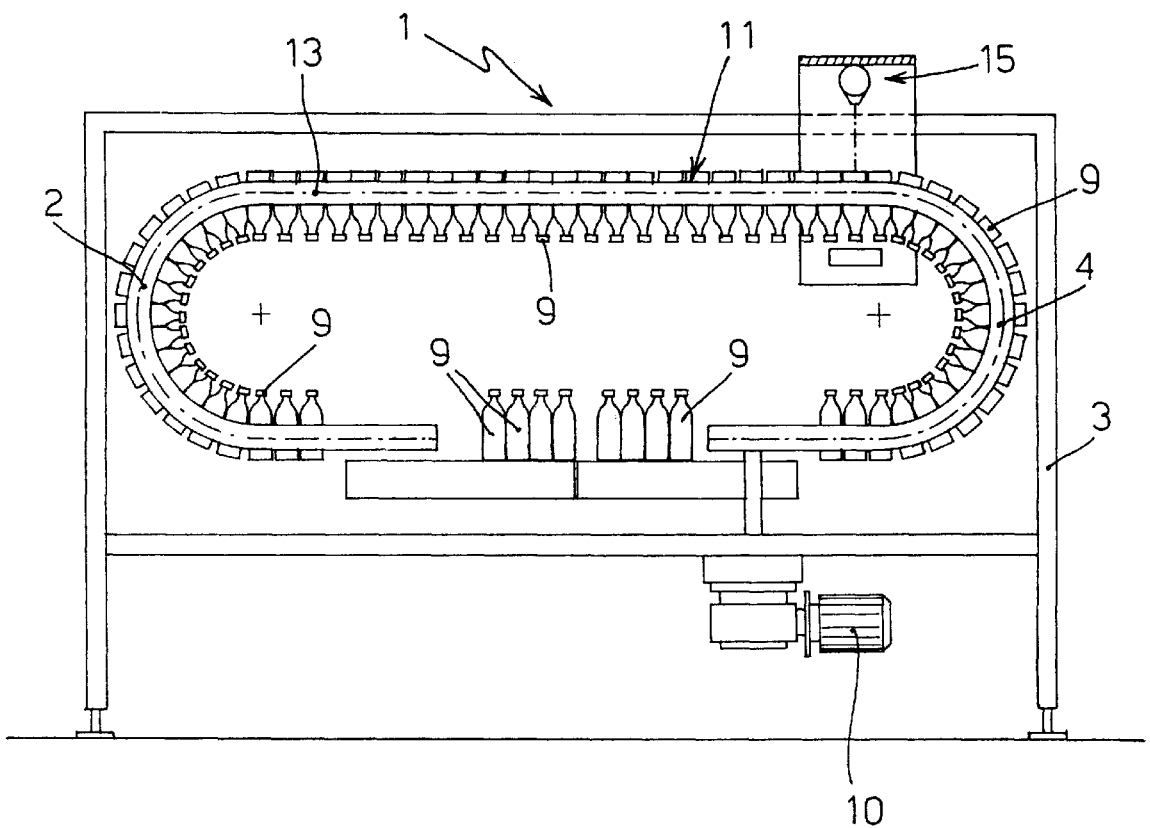
FIG. 1 is a schematic side view of an inspecting apparatus according to the invention.
Figure 2:
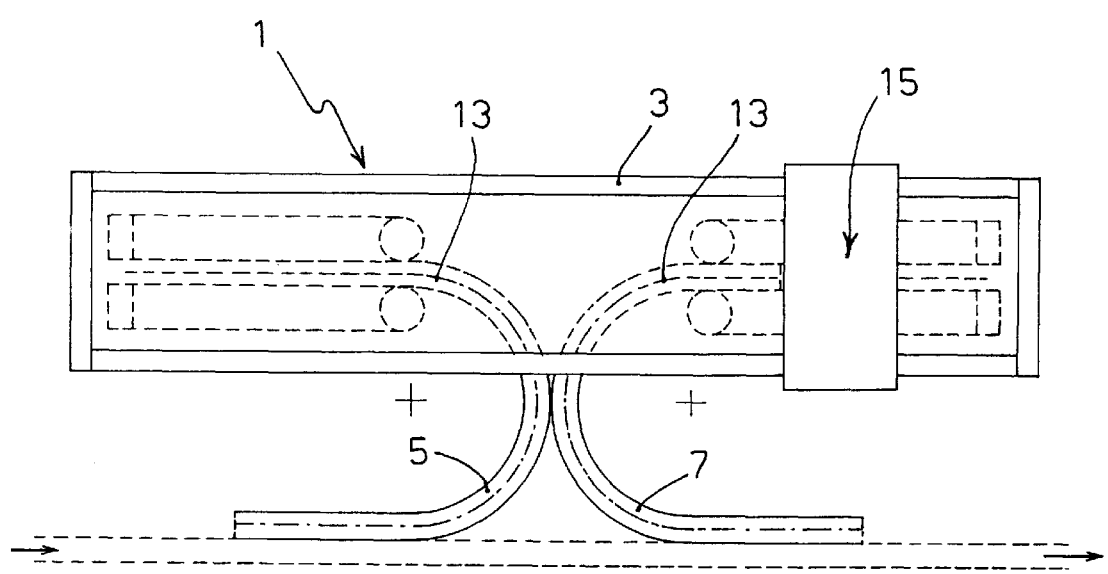
FIG. 2 is a plan view of the apparatus of FIG. 1.

With reference to FIGS. 1 and 2, an inspection apparatus 1 according to the invention comprises a support structure or frame 3 on which a conveyor 13 is mounted, such conveyor being adapted to move a plurality of bottles 9 advancing one after the other in a row.

The conveyor comprises a section 5 for the inlet of the bottles into the conveyor, and a section 7 for their outlet, in both sections 5 and the bottles being moved in an upright position, and a path section 11 extending horizontallly, disposed above the inlet and outlet sections, with the bottles 9 that are conveyed bottom up along this horizontal path 11.

An X-ray inspection unit or device 15 is disposed along said horizontal path, preferably near its end. Preferably, the device 15 emits a radiation that is substantially parallel to the axes of the bottles 9.

Between the horizontal path 11 and the bottle inlet and outlet, there are provided two arcuate connecting sections, respectively a curved section 2 for the connection to the inlet and a curved section 4 for the connection to the outlet. The two connecting sections 2 and 4 extends vertically and the bottle advancing direction changes by 180° with respect to a horizontal axis. In the illustrated embodiment, the two connecting sections 2 and 4 are formed as arcs of a circle lying in a vertical plane, however this is not to be meant as limiting. Moreover, in the illustrated embodiment, sections 5 and 7 are formed as semicircumferential connecting sections lying in a horizontal plane. Suitable conveyors adapted to hold the vessels also in a tilted or upside-down orientation are known, for example, in plants for bottle washing, and are not further disclosed with details. A motor 10 drives in a known manner the different sections of conveyor 13.

Thanks to the configuration of the apparatus according to the invention, a satisfactoty inspection can be accomplished through a single device for detecting any presence of impurities or contaminants.

Figure 3:
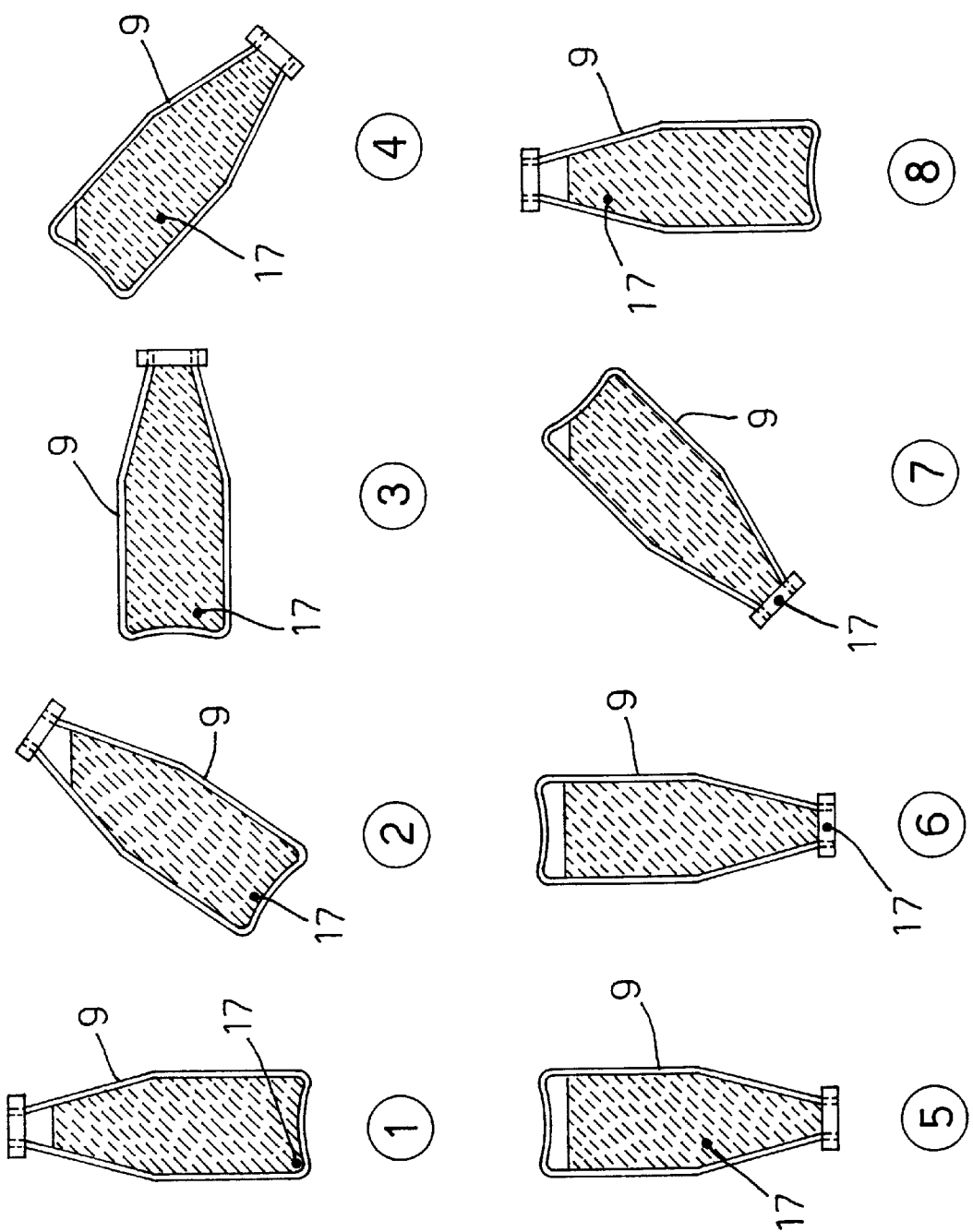
FIG. 3 is a schematic view illustrating several positions of a bottle when advancing along the apparatus according to the invention.

The views of FIG. 3 illustrate a series of different positions of a bottle along the conveyor with the position of an impurity 17 marked both with respect to the liquid and to the bottle.

As shown in the Figures, such impurity is initially deposited on the bottom of the bottle, and therefore is in a position difficult to be detected. When the bottle advances in the conveyor the impurity progressively migrates until it settles onto the tap of the upturned bottle. The inspection device 15 radiates the bottle when this latter is in the position indicated by 5 and the impurity is sinking towards the tap.

Indicatively the length of the apparatus is about 4 meters and the width of the upper straight section is in the order of 2.5 meters, with the device 15 being positioned slightly before the start of the arcuate connecting section 4.

The apparatus according to the invention allows for the following advantages.

An improvement of the inspection performance since the glass thickness to be considered is at least half of the standard thickness with a side viwepoint, and since the thickness changes in such area are much reduced and allow the inspection of an image gradient practically null.

The use of a small size sensor and having a higher resolution with lower costs since the radiation is concentrated in a more limited volume.

What is claimed is:

1. An apparatus for non-destructive X-ray inspection of liquid foodstuffs contained in glass containers having a bottom portion and a tap portion comprising:

a conveyor along which a plurality of such containers is moved, having a horizontal path, a section for the inlet and a section for the outlet of said containers, and a device disposed along said horizontal path for inspecting said containers and detecting the presence of contaminants in said liquid;

said conveyor further comprising a first arcuate section connecting said inlet section with said horizontal path and extending in a vertical direction with the cotainer advancing direction varying by 180° with respect to a horizontal axis; and a second arcuate section connecting said outlet section with said horizontal path and extending in a vertical direction with the cotainer advancing direction varying by 180° with respect to a horizontal axis;

said conveyor being further provided with means for holding the containers even when these latter advance in a tilted or upside down orientation, wherein said inspection device is disposed at the end of said horizontal path along which said containers are conveyed in an upturned position and wherein said inspection device is arranged to inspect said tap portion of the containers.

2. An apparatus as claimed in claim 1 wherein said horizontal path is located over said arcuate connecting sections.

3. An apparatus as claimed in claim 1, wherein said first and second arcuate connecting sections are formed as arcs of a circle lying in a vertical plane.

4. An apparatus as claimed in claim 3, wherein said sections for the inlet and the outlet of said vessels are formed with semi-circumferential connecting sections lying in a horizontal plane.

5. An apparatus as claimed in claim 2, wherein said first and second arcuate connecting sections are formed as arcs of a circle lying in a vertical plane.

\* \* \* \* \*